US007228658B2

(12) United States Patent
Hirahara et al.

(10) Patent No.: US 7,228,658 B2
(45) Date of Patent: Jun. 12, 2007

(54) METHOD OF ATTACHING AN END SEAL TO MANUFACTURED SEEDS

(75) Inventors: Edwin Hirahara, Federal Way, WA (US); Paul G. Gaddis, Seattle, WA (US)

(73) Assignee: Weyerhaeuser Company, Federal Way, WA (US)

( * ) Notice: Subject to any disclaimer, the term of this patent is extended or adjusted under 35 U.S.C. 154(b) by 306 days.

(21) Appl. No.: 10/912,909

(22) Filed: Aug. 5, 2004

(65) Prior Publication Data

US 2005/0045089 A1 Mar. 3, 2005

Related U.S. Application Data

(60) Provisional application No. 60/560,710, filed on Aug. 27, 2003.

(51) Int. Cl.
*A01C 1/04* (2006.01)
(52) U.S. Cl. .......................... 47/57.6; 504/100; 53/404
(58) Field of Classification Search ................. 47/57.6; 504/100; 53/403, 404, 79, 469
See application file for complete search history.

(56) References Cited

U.S. PATENT DOCUMENTS

| | | | |
|---|---|---|---|
| 2,309,702 A | 2/1943 | Kirschenbaum |
| 2,502,809 A | 4/1950 | Vogelsang |
| 2,809,772 A | 10/1957 | Weisz |
| 3,034,905 A | 5/1962 | Weintraub et al. |
| 3,098,320 A | 7/1963 | Estkowski |
| 3,545,129 A | 12/1970 | Schreiber et al. |
| 3,688,437 A | 9/1972 | Hamrin |
| 3,690,034 A | 9/1972 | Knapp |
| 3,734,987 A | 5/1973 | Hamrin |
| 3,850,753 A | 11/1974 | Chibata et al. |
| 4,147,930 A | 4/1979 | Browne et al. |
| 4,166,006 A | 8/1979 | Hertl et al. |
| 4,252,827 A | 2/1981 | Yokoyama et al. |
| 4,465,017 A | 8/1984 | Simmons |
| 4,562,663 A | 1/1986 | Redenbaugh |
| 4,583,320 A | 4/1986 | Redenbaugh |
| 4,615,141 A | 10/1986 | Janick et al. |

(Continued)

FOREIGN PATENT DOCUMENTS

CA 1241552 9/1988

(Continued)

OTHER PUBLICATIONS

Adlercreutz, P., and B. Mattiasson, "Oxygen Supply to Immobilized Biocatalysts. A Model Study," *Acta Chem. Scand.* B36:651-653, 1982.

(Continued)

*Primary Examiner*—Jeffrey L. Gellner
(74) *Attorney, Agent, or Firm*—Christensen O'Connor Johnson Kindness (57) ABSTRACT

A method of attaching an end seal to a manufactured seed is provided. The method includes providing a manufactured seed having an open end and inflating a sealing material to form an enclosure having an interior surface. The method also includes placing the enclosure into contact with the open end of the manufactured seed and attaching the enclosure to the manufactured seed to seal the open end of the manufactured seed.

19 Claims, 8 Drawing Sheets

U.S. PATENT DOCUMENTS

| | | | |
|---|---|---|---|
| 4,628,633 | A | 12/1986 | Nilsson |
| 4,665,648 | A | 5/1987 | Branco et al. |
| 4,715,143 | A | 12/1987 | Redenbaugh et al. |
| 4,769,945 | A | 9/1988 | Motoyama et al. |
| 4,777,762 | A | 10/1988 | Redenbaugh et al. |
| 4,777,907 | A | 10/1988 | Sänger |
| 4,779,376 | A | 10/1988 | Redenbaugh |
| 4,780,987 | A | 11/1988 | Nelsen et al. |
| 4,802,305 | A | 2/1989 | Kojimoto et al. |
| 4,802,905 | A | 2/1989 | Spector |
| 4,806,357 | A | 2/1989 | Garrett et al. |
| 4,808,430 | A | 2/1989 | Kouno |
| 4,866,096 | A | 9/1989 | Schweighardt |
| 4,879,839 | A | 11/1989 | Gago et al. |
| 4,981,007 | A * | 1/1991 | Shima et al. .............. 53/432 |
| 5,010,685 | A | 4/1991 | Sakamoto et al. |
| 5,044,116 | A | 9/1991 | Gago et al. |
| 5,181,259 | A | 1/1993 | Rorvig |
| 5,183,757 | A | 2/1993 | Roberts |
| 5,236,469 | A | 8/1993 | Carlson et al. |
| 5,250,082 | A | 10/1993 | Teng et al. |
| 5,258,132 | A | 11/1993 | Kamel et al. |
| 5,284,765 | A | 2/1994 | Bryan et al. |
| 5,427,593 | A | 6/1995 | Carlson et al. |
| 5,451,241 | A | 9/1995 | Carlson et al. |
| 5,464,769 | A | 11/1995 | Attree et al. |
| 5,529,597 | A | 6/1996 | Iijima |
| 5,564,224 | A | 10/1996 | Carlson et al. |
| 5,565,355 | A | 10/1996 | Smith |
| 5,666,762 | A | 9/1997 | Carlson et al. |
| 5,680,320 | A | 10/1997 | Helmer et al. |
| 5,687,504 | A | 11/1997 | Carlson et al. |
| 5,701,699 | A | 12/1997 | Carlson et al. |
| 5,732,505 | A | 3/1998 | Carlson et al. |
| 5,771,632 | A | 6/1998 | Liu et al. |
| 5,784,162 | A | 7/1998 | Cabib et al. |
| 5,799,439 | A | 9/1998 | MacGregor |
| 5,821,126 | A | 10/1998 | Durzan et al. |
| 5,842,150 | A | 11/1998 | Renberg et al. |
| 5,877,850 | A | 3/1999 | Ogata |
| 5,930,803 | A | 7/1999 | Becker et al. |
| 5,960,435 | A | 9/1999 | Rathmann et al. |
| 6,021,220 | A | 2/2000 | Anderholm |
| 6,092,059 | A | 7/2000 | Straforini et al. |
| 6,119,395 | A | 9/2000 | Hartle et al. |
| 6,145,247 | A | 11/2000 | McKinnis |
| 6,470,623 | B1 | 10/2002 | Hirahara |
| 6,567,538 | B1 | 5/2003 | Pelletier |
| 6,582,159 | B2 | 6/2003 | McKinnis |
| 2002/0055615 | A1 | 5/2002 | Zhang et al. |
| 2002/0192686 | A1 | 12/2002 | Adorjan et al. |

FOREIGN PATENT DOCUMENTS

| | | | |
|---|---|---|---|
| CA | 1250296 | | 2/1989 |
| EP | 0 107 141 | A1 | 5/1984 |
| EP | 0 300 730 | A1 | 1/1989 |
| EP | 0 380 692 | A1 | 8/1990 |
| EP | 0776601 | A1 | 6/1997 |
| FR | 2 680 951 | A1 | 3/1993 |
| JP | 61040708 | | 2/1986 |
| JP | 62275604 | | 11/1987 |
| JP | 63133904 | | 6/1988 |
| JP | 63152905 | | 6/1988 |
| JP | 2-46240 | | 2/1990 |
| JP | 407179683 | A | 7/1995 |
| JP | 09313013 | A * | 12/1997 |
| WO | WO 91/00781 | A1 | 1/1991 |
| WO | WO 91/01803 | | 2/1991 |
| WO | WO 92/07457 | A1 | 5/1992 |
| WO | WO 95/05064 | | 2/1995 |
| WO | WO 98/33375 | | 8/1998 |
| WO | WO 99/26470 | | 6/1999 |

OTHER PUBLICATIONS

Adlercreutz, P., and B. Mattiasson, "Oxygen Supply to Immobilized Cells: 1. Oxgen Production by Immobilized *Chlorella pyrenoidosa*," *Enzyme Microbial Technol.* 4:332-336, 1982.

Adlercreutz, P., and B. Mattiasson, "Oxygen Supply to Immobilized Cells. 3. Oxygen Supply by Hemoglobin or Emulsions of Perfluorochemicals," *Eur. J. Appl. Microbiol . & Biotechnol.* 16:165-170, 1982.

Bapat, V.A., "Studies on Synthetic Seeds of Sandalwood (*Santalum album L.*) and Mulberry (*Morus indica L.*)," in K. Redenbaugh (ed.), *Synseeds: Applications of Synthetic Seeds to Crop Improvement*, CRC Press, Inc., Boca Ranton, Fla., 1993, pp. 381-407.

Bapat, V.A., and P.S. Rao, "In Vivo Growth of Encapsulated Axillary Buds of Mulberry (*Morus indica L.*)," *Plant Cell, Tissue and Organ Culture* 20:69-70, 1990.

Bapat, V.A., and P.S. Rao, "Sandalwood Plantlets from 'Synthetic Seeds,'" *Plants Cell Reports* 7:434-436, 1988.

Buchenauer, H., "Mode of Action and Selectivity of Fungicides Which Interfere with Ergosterol Biosynthesis," *Proceedings of the 1977 British Crop Protection Conference—Pests and Diseases*, Brighton, U.K., 1977, pp. 699-711.

Chandler, D., et al., "Effects of Emulsified Perfluorochemicals on Growth and Ultrastructure of Microbial Cells in Culture," *Biotechnol. Letters* 9(3):195-200, 1987.

Cheng, Z., and P.P. Ling, "Machine Vision Techniques for Somatic Coffee Embryo Morphological Feature Extraction," *Americn Society of Agricultural Engineers* 37(5):1663-1669, 1994.

Chi, C.-M., et al., "An Advanced Image Analysis System for Evaluation of Somatic Embryo Development," *Biotechnology and Bioengineering* 50:65-73, Apr. 996.

Clark, Jr., L.C., et al., "Emulsions of Perfluoranted Solvents for Intravascular Gas Transport," *Fed. Proceed.* 34(6):1468-1477, 1975.

Clark, Jr., L.C., et al., "The Physiology of Synthetic Blood," *J.Thorac. & Cardiovasc. Surg.* 60(6):757-773, 1970.

Damiano, D., and S.S. Wang, "Novel Use of Perfluorocarbon for Supplying Oxygen to Aerobic Submerged Cultures," *Biotechnol. Letters* 7(2):81-86, 1985.

Datta, S.K., and I. Potrykus, "Artifical Seeds in Barley: Encapsulation of Microspore-Derived Embryos," *Thero. Appl. Genet.* 77:820-824, 1989.

Dumet, D., et al., "Crytopreservation of Oil Palm (*Elaeis guincesis Jacq.*) Somatic Embyros Involving a Desiccation Step," *Plant Cell Reports* 12:352-355, 1993.

Dupuis, J.-M., et al., "Pharmaceutical Capsules as a Coating System for Artificial Seeds," *Bio/Technol.* 12:385-389, 1994.

Ebert, W.W., and P.F. Knowles, "Inheritance of Pericarp Types, Sterility, and Dwarfness in Several Safflower Crosses," *Crop Science* 6:579-582, 1966.

Fujii, A., et al., "Artificial Seeds for Plant Propagation," *Trends in Bio/Technol.* 5:335-339, 1987.

Fujii, J., et al., "ABA Maturation and Starch Accumulation in Alfalfa Somatic Embryos" (Abstract), In Vitro 25 (3, Part 2):61A, 1989.

Fujii, J., et al., "Improving Plantlet Growth and Vigor From Alfalfa Artificial Seed" (Abstract), In Vitro 24 (3, Part 2):70A, 1989.

Fujita, T., et al., "Fluorocarbon Emulsion as a Candidate for Artificial Blood," *Europ. Surg. Res.* 3:436-453, 1971.

Geyer, R.P., "'Bloodless' Rats Through the Use of Artificial Blood Substitutes," *Fed. Proceed* 34(6):1499-1505, 1975.

Gray, D.J., and A. Purohit, "Somatic Embryogenesis and Development of Synthetic Seed Technology," *Crit. Rev. Plant Sci.* 10(1):33-61, 1991.

Grob, J.A., et al., "Dimensional Model of Zygotic Douglas-Fir Embryo Development," *International Journal of Plant Sciences* 160(4):653-662, 1999.

Gupta, P.K., and D.J. Durzan, "Biotechnology of Somatic Polyembryogenesis and Plantlet Regeneration in Loblolly Pine," *Bio/Technol.* 5:147-151, 1987.

Ibarbia, E.A., "Synthetic Seed: Is It the Future," *Western Grower and Shipper* 59:12, 1988.

Kim YH, "ABA and Polyox-Encapsulation or High Humiduty Increases Survival of Desiccated Somatic Embryos of Celery," *HortScience* 24(4):674-676, 1989.

King, A.T., et al., "Perfluorochemicals and Cell Culture," *Biotechnol.* 7:1037-1042, 1989.

Kitto, S.L., and J. Janick, "A Citrus Embryo Assay to Screen Water-Soluble Resins as Synthetic Seed Coats," *HortScience* 20(1):98-100, 1985.

Kitto, S.L., and J. Janick, "Production of Synthetic Seeds by Encapsulating Asexual Embryos of Carrot," *J. Amer. Soc. Hort. Sci.* 110(2):277-282, 1985.

Li, X.-Q., "Somatic Embryogenesis and Synthetic Seed Technology Using Carrot as a Model System," in K. Redenbaugh (ed.), *Synseeds: Applications of Synthetic Seeds to Crop Improvement*, CRC Press, Inc., Boca Raton, Fla., 1993, pp. 289-304.

Mattiasson, B., and P. Adlercreutz, "Use of Perfluorochemicals for Oxygen Supply to Immobilized Cells," *Ann. N. Y. Acad. Sci.* 413:545-547, 1984.

Paulet, F., et al., "Cryopreservation of Apices of In Vitro Plantlets of Sugarcane (*Saccharum* sp. Hybrids) Using Encapsulation/Dehydration," *Plant Cell Reports* 12:525-529, 1993.

Redenbaugh, K., et al., "Encapsulated Plant Embryos," *Biotechnology in Agriculture*, 1988, pp. 225-248.

Redenbaugh, K., et al., "Encapsulation of Somatic Embryos for Artificial Seed Production" (Abstract), In Vitro 20(2):256-257, 1984.

Redenbaugh, K., et al., "Encapsulation of Somatic Embryos in Synthetic Seed Coats," *HortScience* 22:(5):803-809, 1987.

Redenbaugh, K., et al., "III.3 Artificial Seeds—Encapsulated Somatic Embryos," *Biotech. in Arg. & For.* 17:395-416, 1991.

Redenbaugh, K., et al., "Scale-Up: Artificial Seeds," in Green et al. (eds.), *Plant Tissue and Cell Culture*, Alan R. Liss, Inc., New York, 1987, p. 473-493.

Redenbaugh, K., et al., "Somatic Seeds: Encapsulation of Asexual Plant Embryos," *Bio/Technology* 4:797-801, 1986.

Riess, J.G., and M. Le Blanc, "Perfluoro Compounds as Blood Substitutes," *Angew. Chem. Int. Ed. Engl.* 17(9):621-634, 1978.

Rogers, M., "Synthetic-Seed Technology," *Newsweek*, Nov. 28, 1983.

Sanada, M., et al., "Celery and Lettuce," in M.K. Redenbaugh (ed.), *Synseeds: Application of Synthetic Seeds to Crop Improvement*, CRC Press, Inc., Boca Raton, Fla., 1993, pp. 305-322.

Senaratna, T., "Artificial Seeds," *Biotech Adv.* 10(3)379-392, 1992.

Sharma SK et al., "Novel Compositions of Emulsified Perfluorocarbons for Biological Applications," *Brit. J. Pharmacol.* 89:665P, 1986.

Stuart, D.A., and M.K. Redenbaugh, "Use of Somatic Embryogenesis for the Regeneration of Plants," in H.M. LeBaron et al. (eds.), *Biotechnology in Agricultural Chemistry*, American Chemical Society, Washington, D.C., 1987, pp. 87-96.

Teasdale, R.D., and P.A. Buxton, "Culture of *Pinus radiata* Embryos With Reference to Artificial Seed Production," *New Zealand J. For. Sci.* 16(3):387-391, 1986.

Tessereau, H. et al., "Cryopreservation of Somatic Embryos: A Tool for Germplasm Storage and Commercial Delivery of Selected Plants," *Ann. Bot.* 74:547-555, 1994.

Timmis, R., "Bioprocessing for Tree Production in the Forest Industry: Conifer Somatic Embryogenesis," *Biotechnology Progress* 14(1):156-166, 1998.

Weyerhaeuser, G.H., "Biotechnology in Forestry: The Promise and the Economic Reality" *Solutions! for People, Processes and Paper* 86(10):28-30, Oct. 2003.

* cited by examiner

METHOD OF ATTACHING AN END SEAL TO MANUFACTURED SEEDS

CROSS REFERENCE TO RELATED APPLICATION

The present application claims the benefit of U.S. Provisional Application No. 60/560,710, filed Aug. 27, 2003.

FIELD OF THE INVENTION

The present invention relates generally to manufactured seeds and, more particularly, to a method for attaching an end seal to a manufactured seed.

BACKGROUND OF THE INVENTION

Asexual propagation for plants has been shown for some species to yield large numbers of genetically identical embryos, each having the capacity to develop into a normal plant. Such embryos must usually be further cultured under laboratory conditions until they reach an autotrophic "seedling" state characterized by an ability to produce their own food via photosynthesis, resist desiccation, produce roots able to penetrate soil and fend off soil microorganisms. Some researchers have experimented with the production of artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

Typical manufactured seeds include a seed coat, synthetic gametophyte and a plant embryo. The seed coat typically is a cylindrical capsule having a closed end and an open end. The synthetic gametophyte is placed within the seed coat, such that the gametophyte substantially fills the interior of the seed coat. A longitudinally extending hard porous insert, commonly known as a cotyledon restraint, may be centrally located within the synthetic gametophyte and includes a centrally located cavity extending partially through the length of the cotyledon restraint. The cavity is sized to receive the plant embryo therein. The well known plant embryo includes a radicle end and a cotyledon end. The plant embryo is deposited within the cavity of the cotyledon restraint cotyledon end first. The plant embryo is then sealed within the seed coat by at least one end seal. There is a weakened spot in the end seal to allow the radicle end of the embryo to penetrate the end seal.

Typically, the end seal is formed from a sheet of polymer material. In the past, a mechanical rod is used to stretch and, therefore, thin or weaken a small spot in the center of the seal. The weakened spot in the end seal is desirable because as the embryo begins to grow, the weakened spot permits tangential distribution of load to assist in the breakthrough of the embryo through the end seal.

A disk of predetermined diameter is then cut from the polymer sheet with the weakened spot in the center of the disk forming the end seal. After the end seals are cut from the polymer sheet, they are pushed out of a punch cavity with a rod and then fall by gravity on top of the seed coat. The seed coat with the end seal is then transferred to a separate station to heat fuse the end seals to the seed coats. Although such a process is effective at forming and sealing end seals to the seed coat of a manufactured seed, it is not without its problems.

First, it is difficult to maintain the exact location of the opening into the cavities of the cotyledon restraint as the manufactured seed passes through the production line. Second, the placement of the end seal over the seed coat is not reliable. Additionally, the end seals tend to stick to the punch or punch cavity. Further, fusing of the end seals to the seed coats is difficult and time consuming because the end seals must be heated to a point where the end seal is fused to the seed coat without damaging the dome or weakened area itself. Sometimes the fusing process melts holes in the weakened spot. The fusing process may cause damage to the plant embryo itself. Also, because of how the material was stretched, the resulting thinned or weakened area is not uniform in thickness. As a result, mass production of manufactured seeds is not only time consuming but also expensive.

Thus, there exists a need for a method of manufacturing and attaching an end seal to a seed coat of a manufactured seed that can produce and attach a large number of end seals to a manufactured seed at a relatively low cost, with a high degree of reliability, and without damaging the plant embryo located within the seed coat.

SUMMARY OF THE INVENTION

In accordance with one embodiment of the present invention, a method of attaching an end seal to a manufactured seed is provided. The method includes providing a manufactured seed having an open end, and inflating a sealing material to form an enclosure having an interior surface. The method includes placing the enclosure into contact with the open end of the manufactured seed. The method also includes attaching the enclosure to the manufactured seed to seal the open end of the manufactured seed.

In accordance with another embodiment of the present invention, the method generally includes providing a manufactured seed having an open end, and pressurizing a sealing material having a structural strength to form an enclosure having an interior surface. In accordance with the present embodiment, the method also includes placing the enclosure into contact with the open end of the manufactured seed, and attaching the enclosure to the open end of the manufactured seed by applying a heat source to the enclosure.

In still yet another embodiment of the present invention, a method of attaching an end seal to a manufactured seed includes providing a manufactured seed having an open end, and forming an enclosure having an interior surface by injecting a predetermined first volume of a fluid into a sealing material. The method also includes maintaining the first volume of a fluid within the enclosure for a predetermined period of time, and exhausting a portion of the first volume of fluid within the enclosure to define a predetermined second volume of a fluid within the enclosure. The method of the present embodiment also includes attaching the enclosure to the open end of the manufactured seed by applying a heat source.

The method of attaching an end seal to a manufactured seed, as well as the resulting manufactured seed, formed in accordance with the various embodiments of the present invention has several advantages over currently available methods. The method of the present disclosure is more accurate because it defines a predetermined burst strength over a wider area of the enclosure. Also, the problem of misaligning end seals with the openings of manufactured seeds is minimized because a larger area of the enclosure is sized to the predetermined burst strength.

Thus, a method of attaching end seals to a manufactured seed in accordance with the various embodiments of the present invention has a high degree of reliability, is able to precisely locate and mass produce end seals, and reliably attaches the end seals to a seed coat.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
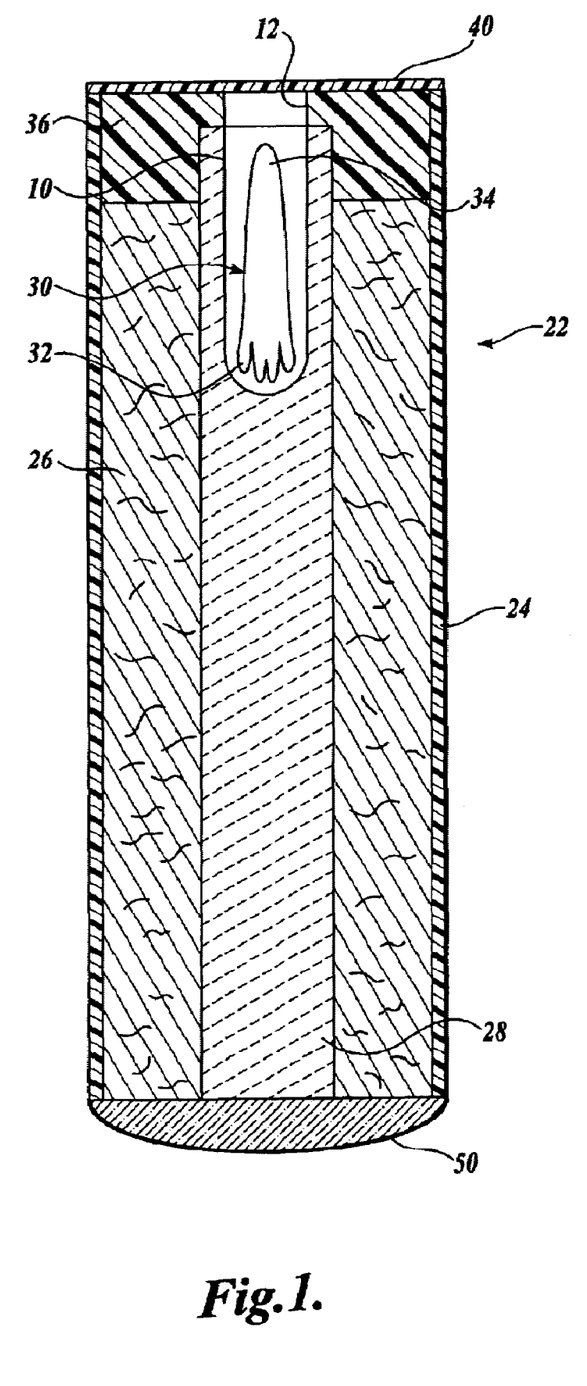
FIG. 1 is a cross-sectional side view of a manufactured seed with an end seal formed in accordance with various embodiments of the present invention.
Figure 2:
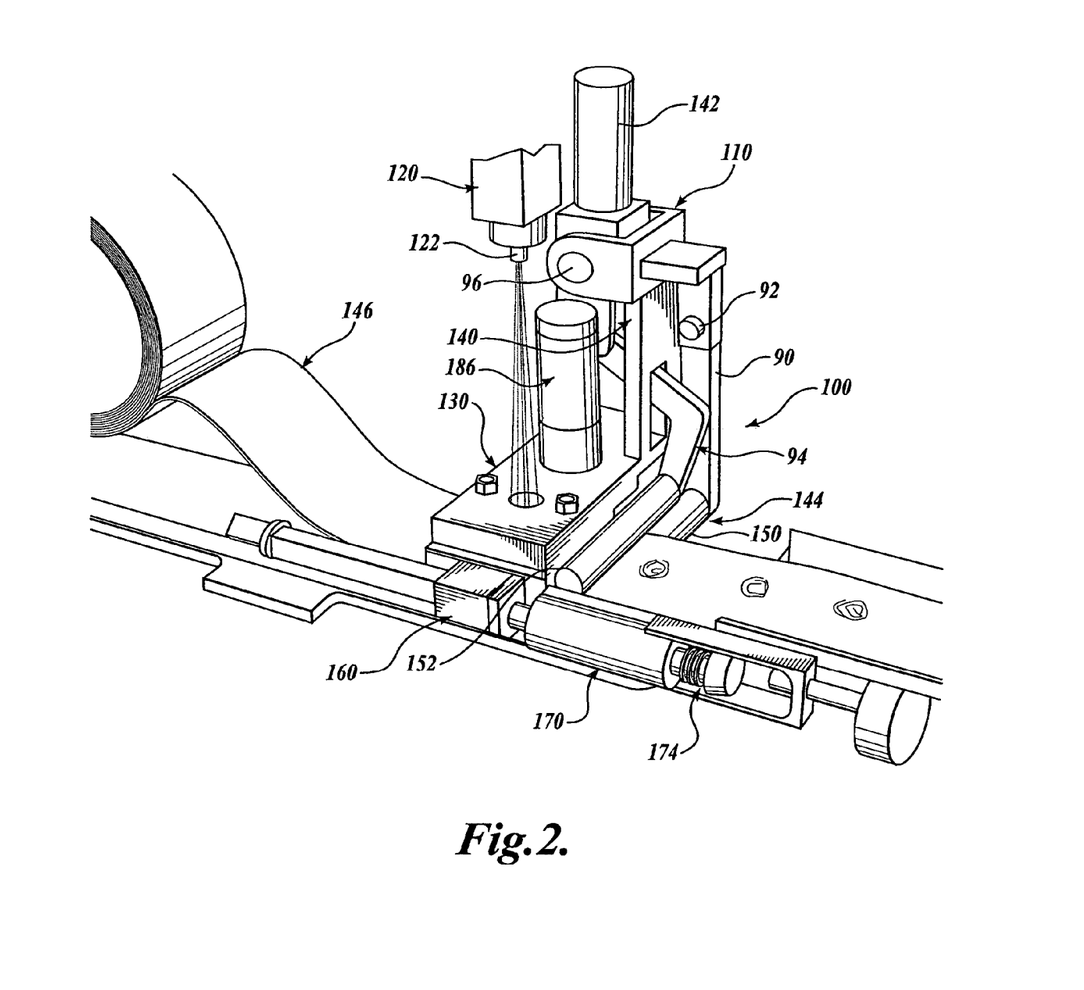
FIG. 2 is a perspective view of an apparatus used to manufacture and attach an end seal to a manufactured seed in accordance with various embodiments of the present invention.

FIG. 1 illustrates an end seal 40 constructed in accordance with certain embodiments of the present invention for a manufactured seed 22. As is disclosed in U.S. Pat. No. 5,701,699, issued to Carlson et al., the disclosure, which is hereby expressly incorporated by reference, well known manufactured seeds 22 include a seed coat 24, synthetic gametophyte 26, a cotyledon restraint 28, a plant embryo 30, a primary end seal 36, and a secondary end seal 50. The cotyledon restraint 28 is suitably manufactured from a hard porous material and includes a longitudinally extending cavity 10. The cavity 10 extends through the primary end seal 36 and partially through one end of the cotyledon restraint 28. The open end of the cavity 10 is known as a cotyledon restraint opening 12. The cavity 10 is sized to receive the plant embryo 30 therein. The plant embryo 30 includes a cotyledon end 32 and a root end 34.

The end seal 40 seals the cotyledon restraint opening 12. The end seal 40 is formed from a sheet of polymeric sealing material, such as Parafilm®. Parafilm® is a well-known moisture-proof, self-sealing flat wrapper sold by American National Can Company Corporation of Chicago, Ill. The end seal 40 has a substantially uniform thickness when viewed in cross section. While it is preferred that the end cap 40 has a substantially uniform thickness, other embodiments, such as end seals having a nonuniform thickness, are also within the scope of the present invention.

An end seal assembly 100 used in the formation and attachment of an end seal 40 to a manufactured seed 22 is best seen by referring to FIGS. 2–6. The end seal assembly 100 includes a sealing material advancement assembly 110, a sealing assembly 120, and an end seal formation and attachment assembly 130.

The sealing assembly advancement assembly 110 includes a frame 140, a pneumatic cylinder 142, advancement rollers 144, and a source of sealing material 146. The pneumatic cylinder 142 is operatively connected to the advancement rollers 144. The advancement rollers 144 include first and second roller bars 150 and 152. The first roller bar 150 is attached to a first pivot link 90 and is pivotably connected to the frame 140 at a first pivot point 92. The second roller bar 152 is connected to one end of a second pivot link 94 and pivots about a second pivot point 96 for selective advancement of the sealing material 146.

In the illustrated embodiment, the sealing material 146 is pinned between opposing surfaces of the first and second rollers 150 and 152. After formation of the end seal 140, as is described in greater detail below, the pneumatic cylinder 142 is actuated to selectively advance the sealing material 146 relative to the end seal formation and attachment assembly 130 by pivoting the first and second pivot links 90 and 94 about their respective pivot points 92 and 96.

The sealing assembly 120 is a well-known heat generator, such as a laser, and includes an emitter 122. The sealing assembly 120 is disposed above the end seal formation and attachment assembly 130 and is positioned to seal and cut the end seal 40 to a manufactured seed 20, as is described in greater detail below.

Still referring to FIGS. 2–6, the end seal formation and attachment assembly 130 will now be described in greater detail. The end seal formation and attachment assembly 130 includes a blower assembly 160, a clamping assembly 162, and a main cylinder 164. The blower assembly 160 includes a pneumatically operated cylinder 170 in fluid communication with a first air passageway 172 extending through a portion of the blower assembly 160. The blower assembly 160 may include a volume control assembly 174. The volume control assembly 174, which is suitably a torque thumb screw, selectively sets the amount of fluid within the cylinder 170 used in the process of creating the end seal 40. In that regard, by adjusting the volume control assembly 174, the volume within the cylinder 170 is either increased or decreased, thereby controlling the volume of air used in the creation of the end seal 40.

Figure 3:
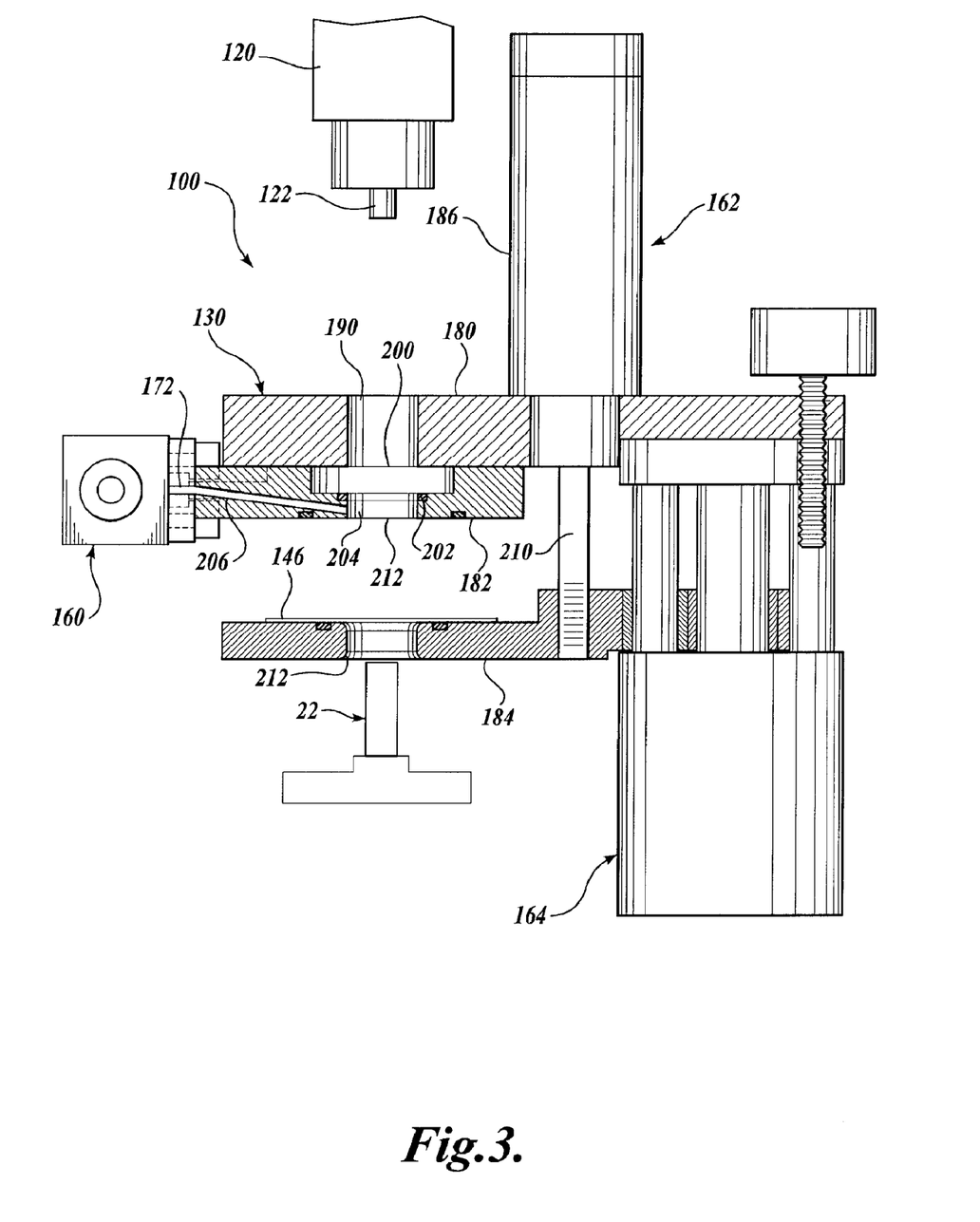
FIG. 3 is a cross-sectional, side planar view of the apparatus of FIG. 2, showing the apparatus in an open position.

As may be best seen by referring to FIG. 3, the clamping assembly 162 includes a top plate 180, a lens plate 182, and a clamp plate 184 operatively connected to a clamp cylinder 186. The top plate 180 is substantially rectangular in configuration and includes a bore 190 extending therethrough. The bore 190 is positioned below emitter 122 of the sealing assembly 120 and is suitably located adjacent the lens plate 182.

The lens plate 182 includes, in one embodiment, a laser lens 200 seated within a cavity extending partially through the lens plate 182. A suitable O-ring 202 seals the laser lens 200 within the cavity of the lens plate 182. The lens plate 182 also includes a bore 204 extending between the lower surface of the cavity and the lower surface of the laser plate 182. The bore 204 is also in fluid communication with a second air passageway 206 extending between the bore 204 and a side of the lens plate 182. The second air passageway 206 is in fluid communication with the first air passageway 172 of the blower assembly 160.

The clamp plate 184 is connected to a piston 210 of the clamp cylinder 186. The clamp plate 184 is suitably a rectangular member and also includes a bore 212 extending through the clamp plate 184. The sealing material 146 is suitably located on the clamp plate 184 and is located above the bore 212.

Figure 4:
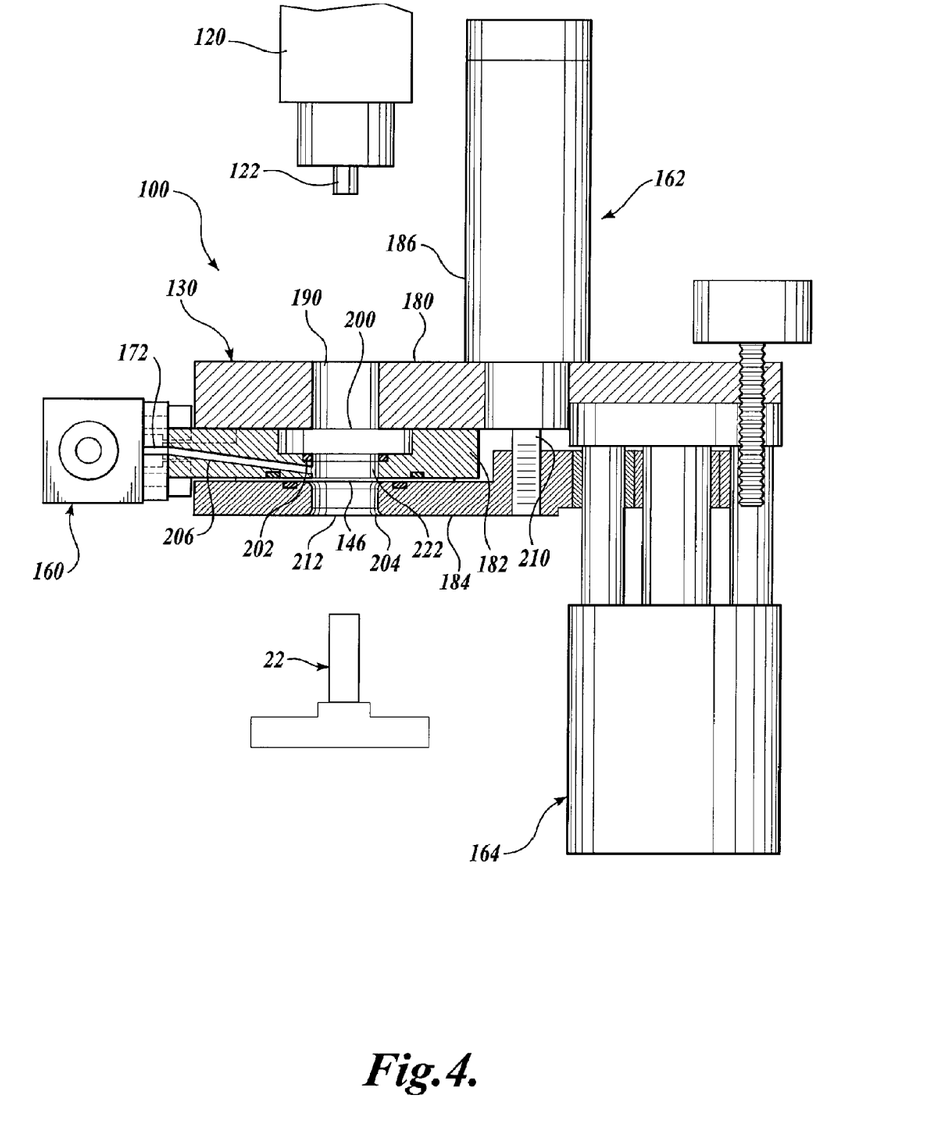
FIG. 4 is a cross-sectional, side planar view of the apparatus of FIG. 3, showing a portion of the apparatus in a clamped position.
Figure 5:
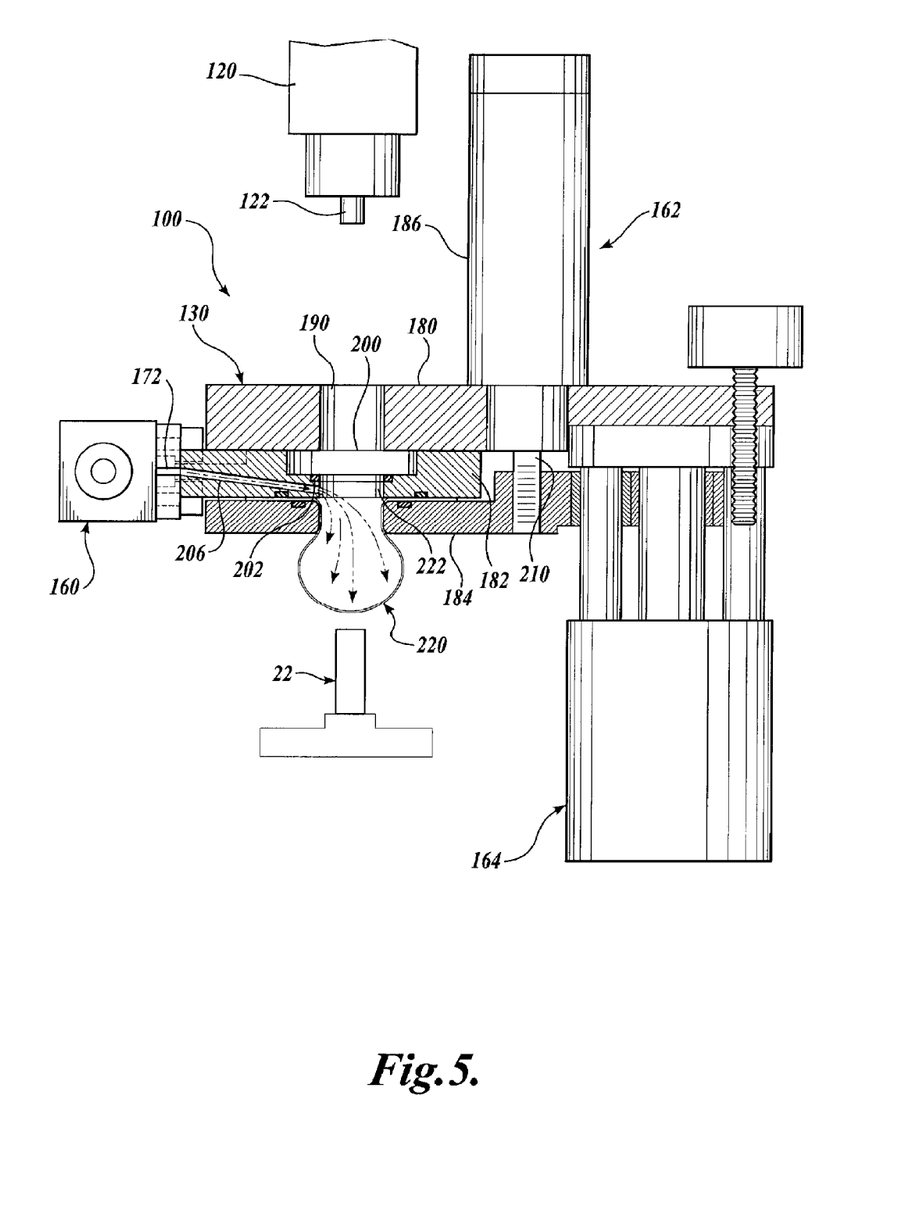
FIG. 5 is a cross-sectional, side planar view of the apparatus of FIG. 4, showing the formation of an enclosure in accordance with certain embodiments of the present invention.

As may be best seen by referring to FIG. 4, when the clamping assembly 162 is displaced into the clamped position, the clamp plate 184 is urged upwardly against the lower surface of the lens plate 182, such that a sealed chamber 122 is formed by the lower surface of the laser lens 200 and the upper surface of the sealing material 146. After the sealing material 146 is clamped between the lens plate 182 and the clamp plate 184, air is transferred from the blower assembly 160 through the first and second air passageways 172 and 206 to form an enclosure 220, as seen in FIG. 5.

The enclosure 220 is bubble-like in configuration and is created by the in-flow of air into the chamber 222. As air is dispensed into the chamber 222, the pressurization causes the sealing material 146 to stretch and thin in the area of the sealing material 146 forming the enclosure 220. Specifically, as the enclosure 220 expands or inflates, the thickness of the sealing material 146 thins to a predetermined burst strength. At this predetermined burst strength, and after the enclosure 220 is attached to the manufactured seed 22 to form the end seal 40, an embryo 30 germinating within the cavity 12 of the manufactured seed 22 will break through the end seal 40 at the desired burst strength. Verification of the burst strength is obtained by well-known penetrometers.

Although it is preferred that air is the preferred medium to create the enclosure 220, it should be apparent that other fluid or gaseous media are also within the scope of the present invention. As a nonlimiting example, the medium used to create the enclosure 220 also includes liquids, such as water. Further, as used within the context of the present invention, the term "enclosure" includes not only bubble-like structures, but also any equivalent structure, such as a preformed cap made from the sealing material 146 or similar material. Accordingly, such enclosures are also within the scope of the present invention.

Figure 6:
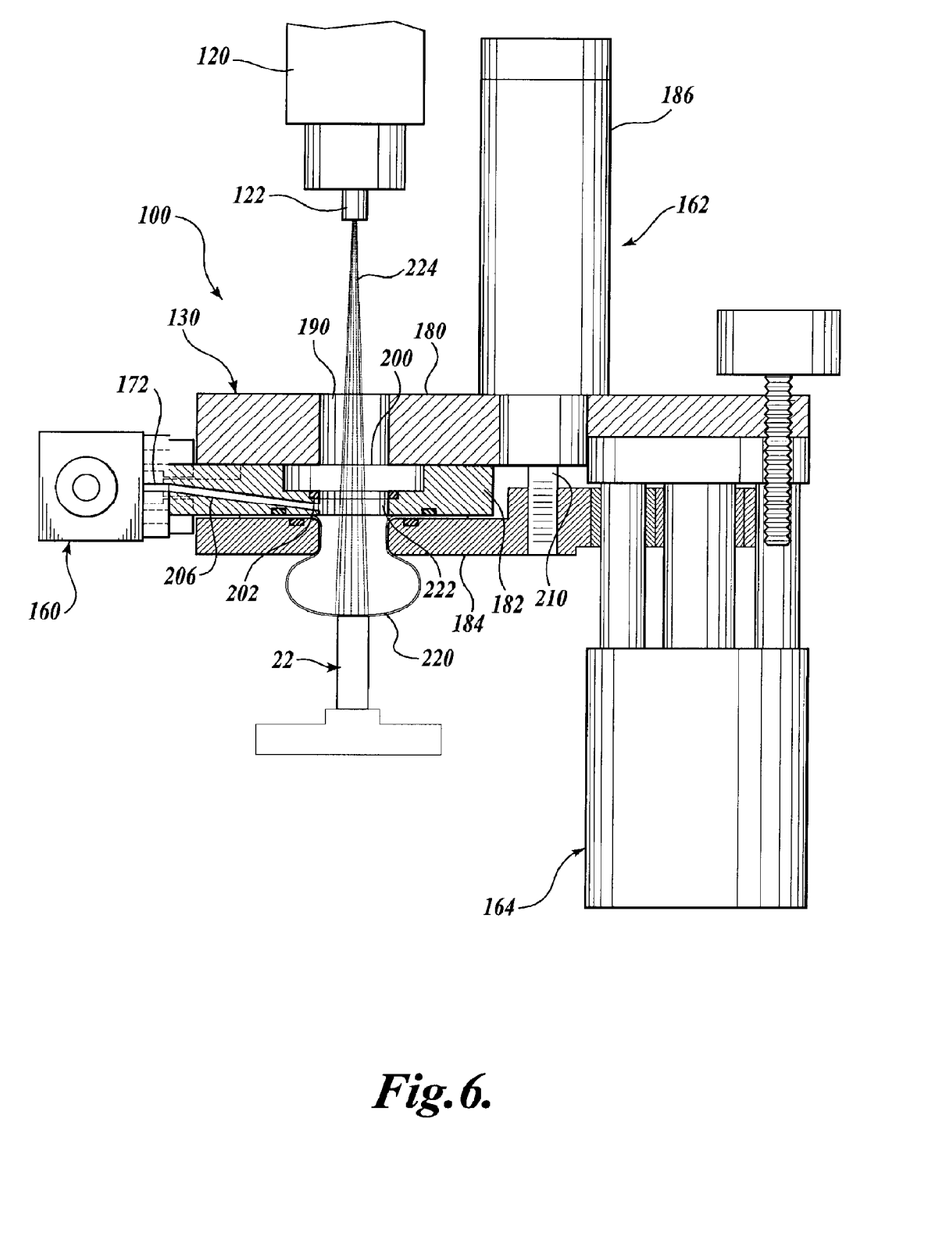
FIG. 6 is a cross-sectional, side planar view of the apparatus of FIG. 5, showing attachment of an enclosure to a manufactured seed in accordance with one embodiment of the present invention.

As may be best seen by referring to FIG. 6, after the enclosure 220 is formed, the main cylinder 164 selectively displaces the enclosure 220 into contact with the manufactured seed 22. Thereafter, a heat source 224 is applied to an interior surface of the enclosure 220 to seal a portion of the enclosure 220 to the manufactured seed 22, thereby forming the end seal 40. Suitably, the heat source 224 may also simultaneously or sequentially cut a disk-shaped portion of the enclosure 220 as it seals it to the manufactured seed 22.

In one embodiment of the present invention, the heat source 224 is suitably a laser beam from a well-known laser. As previously noted, it should be apparent that other heat sources, such as devices that fuse the enclosure 220 to the manufactured seed 22, are also within the scope of the present invention. Further still, it should be apparent to one of ordinary skill in the art that the main cylinder 164 may either selectively displace the enclosure 220 into contact with the manufactured seed 22, or move the manufactured seed 22 into contact with the enclosure 220. Accordingly, such embodiments are also within the scope of the present invention.

A summary of the method of the present embodiment is best understood by referring to FIGS. 2–6. In that regard, a sheet of sealing material 146 is clamped between a clamp plate 184 and a lens plate 182. A predetermined volume of fluid fills a cavity 222 formed by the bore 204 and the upper surface of the sealing material 146. As the predetermined volume of fluid is dispensed into the chamber 222, a portion of the sealing material 146 expands to form an enclosure 220. As the enclosure 220 is formed, it reduces the thickness of the sealing material 146 forming the enclosure to a substantially constant thickness. As a result, the enclosure 220 has a predetermined burst strength.

After the formation of the enclosure 220, it is selectively displaced into contact with a manufactured seed 22. Thereafter, a heat source 224 is applied to an interior surface of the enclosure 220 to seal and cut away a portion of the enclosure 220, thereby forming an end seal 40. It should be apparent to one of ordinary skill in the art that the predetermined volume of fluid used to form the enclosure 220 to achieve the preferred burst strength is a function of the type of sealing material 146 selected to form the enclosure 220. As a nonlimiting example, for Parafilm®, a preferred volume of fluid is between 1.96 mm$^3$ and 6,642 mm$^3$. In another nonlimiting example, the predetermined volume is suitably 25.25 mm$^3$.

Figure 7:
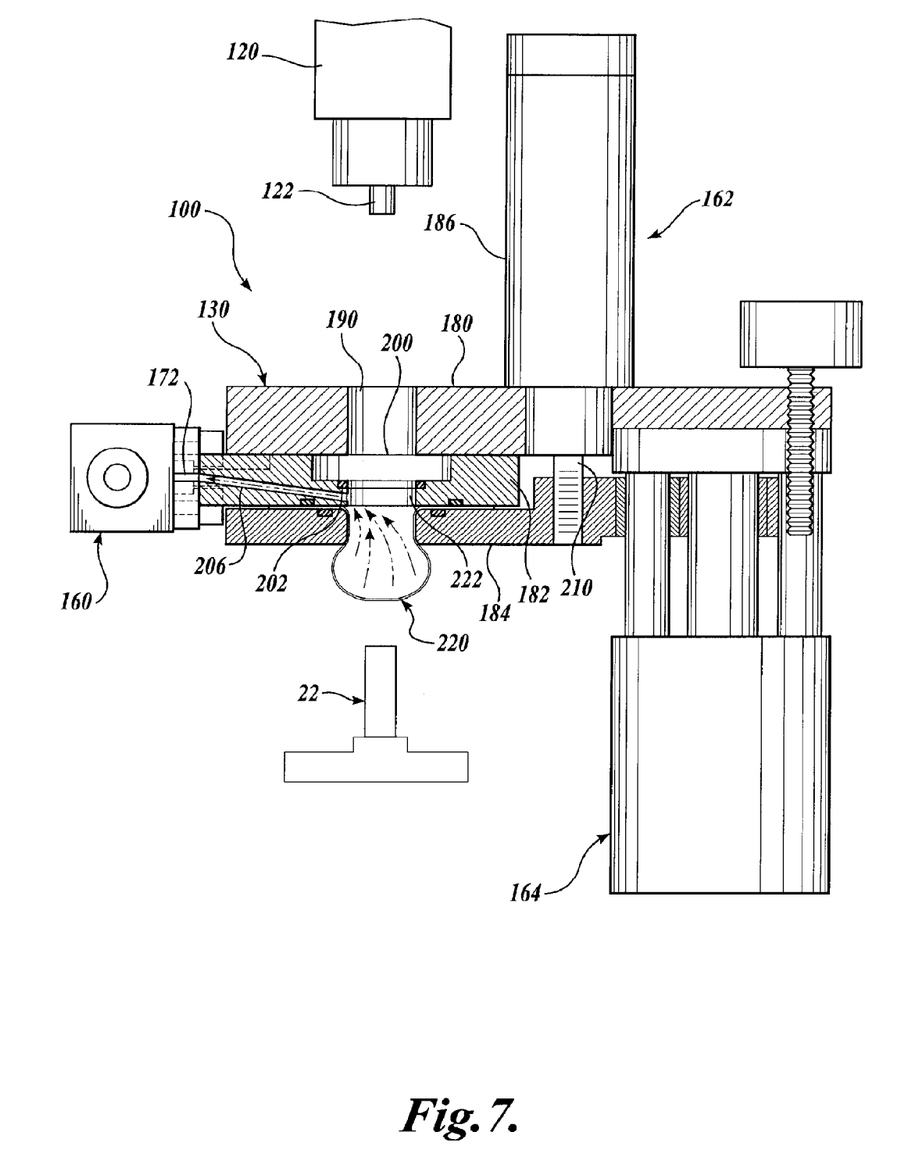
FIG. 7 is a cross-sectional, side planar view of the apparatus of FIG. 4, showing the formation of an enclosure in accordance with another embodiment of the present invention.
Figure 8:
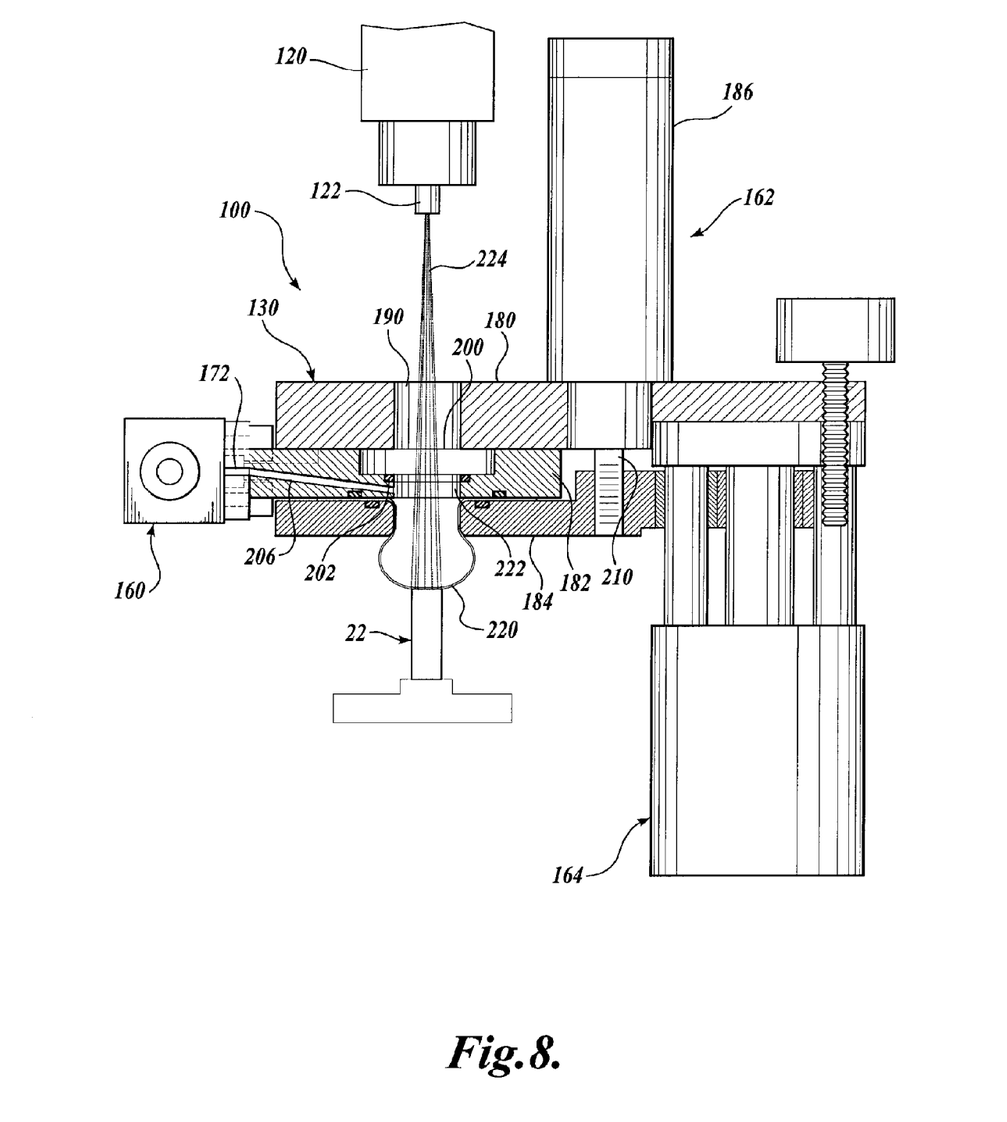
FIG. 8 is a cross-sectional, side planar view of the apparatus of FIG. 7, showing the attachment of an enclosure to a manufactured seed in accordance with another embodiment of the present invention.

Referring now to FIGS. 7 and 8, an alternate embodiment of forming and attaching an end seal 40 in accordance with the present invention will now be described in greater detail. All apparatuses and materials described above for the first embodiment are identical for the present embodiment with one notable difference. Specifically, forming an enclosure 220 in accordance with the present embodiment includes forming an enclosure 220 by providing a first volume of air, waiting a predetermined period of time, and then allowing a portion of the first volume of air to exhaust out from the enclosure 220 to define a predetermined second volume of air within the enclosure 220. Thereafter, a portion of the enclosure 220 is sealed and attached to the manufactured seed 22 in a manner described above and shown in FIG. 8.

Thus, the present embodiment includes dispensing a predetermined first volume of fluid into the enclosure 220. The first volume of fluid is between the range of 1600 mm$^3$ to 8200 mm$^3$. Then, wait a predetermined period of time. This predetermined period of time is suitably between a range of one second to 20 seconds. As a specific, nonlimiting example, the predetermined period of time is three seconds. Thereafter, a predetermined portion of fluid is extracted from within the enclosure 220 to define a second volume of air, suitably between the range of 0 mm$^3$ to 6600 mm$^3$.

As a specific example of the present embodiment, the enclosure 220 is inflated with a first volume of air equal to approximately 3300 mm$^3$. After three seconds, approximately 820 mm$^3$ of air is removed, thereby leaving a second volume of fluid of approximately 2480 mm$^3$ within the enclosure 220. Then, the enclosure 220 is displaced into contact with and sealed to the manufactured seed as described above for the previous embodiments.

From the foregoing description, it can be seen that the manufacture and attachment of an end seal to a manufactured seed formed in accordance with the embodiments of the present invention incorporate many novel features and offer significant advantages over currently available systems. While the presently preferred embodiments of the invention have been illustrated and described, it is to be understood that, within the scope of the appended claims, various changes can be made therein without departing from the spirit of the invention. As a nonlimiting example, an increase in the ambient temperature during the formation of the enclosure reduces the amount of time required between the steps of creating the enclosure and attaching the enclosure to the manufactured seed.

As a further nonlimiting example, the method of the present application may be applied to structures other than manufactured seeds. In that regard, the method may be used to apply a layer of sealing material to one or both sides of a precut, corrugated box container blank. In such a method, a layer of sealing material may be inflated to form an enclosure having a diameter large enough to envelope one side of the container blank. After the enclosure is displaced into contact with one side of the container blank, a laser may seal the portion of the sealing material in contact with the container blank by either selectively applying a laser beam to predetermined areas of the sealing material, or applying a laser across the entire surface area of the sealing material in contact with the container blank. It should be apparent that, like the previously described embodiments, other methods of attaching the sealing material, such as heat treatment, are also within the scope of the present invention.

After the sealing material is attached to the container blank, the laser cuts and trims the sealing material around the perimeter of the container blank. If desired, the container blank may be turned upside down and the method of attaching the sealing material to the unsealed side of the container blank may be applied.

As still yet another nonlimiting example, the method of the present invention may also be applied to test tubes, food containers, paper substrates, application of optical coatings to lenses, and other types of clinical and medical instruments to seal such instruments. For such objects, the method is identical for that described above for the preferred embodiments, with the exception that the manufactured seed is replaced by the object. Accordingly, such embodiments are also within the scope of the present invention.

The embodiments of the invention in which an exclusive property or privilege is claimed are defined as follows:

1. A method of attaching an end seal to a manufactured seed, comprising:
   providing a manufactured seed having an open end;
   inflating a sealing material to form an enclosure having an interior surface;
   placing the enclosure into contact with the open end of the manufactured seed; and
   attaching the enclosure to the manufactured seed to seal the open end of the manufactured seed.

2. The method of attaching an end seal to a manufactured seed of claim 1, wherein the enclosure is formed by inflating the sealing material with a predetermined first volume of a gas.

3. The method of attaching an end seal to a manufactured seed of claim 2, further comprising maintaining the first volume of a gas within the enclosure for a predetermined period of time.

4. The method of attaching an end seal to a manufactured seed of claim 3, further comprising exhausting a portion of the first volume of a gas within the enclosure to define a predetermined second volume of a gas within the enclosure.

5. The method of attaching an end seal to a manufactured seed of claim 4, wherein the first volume of gas expands a thickness of the sealing material to define a predetermined burst strength of the sealing material.

6. The method of attaching an end seal to a manufactured seed of claim 4, wherein attaching the enclosure to the manufactured seed includes applying a heat source to the interior surface of the enclosure.

7. The method of attaching an end seal to a manufactured seed of claim 6, wherein the heat source is a laser.

8. The method of attaching an end seal to a manufactured seed of claim 1, wherein the enclosure includes a substantially constant thickness.

9. The method of attaching an end seal to a manufactured seed of claim 1, wherein attaching the enclosure to the manufactured seed includes applying a laser beam to the interior surface of the enclosure.

10. The method of attaching an end seal to a manufactured seed of claim 9, wherein the enclosure is formed by inflating the sealing material with a predetermined volume of a gas.

11. A method of attaching an end seal to a manufactured seed, comprising:
    providing a manufactured seed having an open end;
    pressurizing a sealing material having a structural strength to form an enclosure having an interior surface;
    placing the enclosure into contact with the open end of the manufactured seed; and
    attaching the enclosure to the open end of the manufactured seed by applying a heat source to the enclosure.

12. The method of attaching an end seal to a manufactured seed of claim 11, wherein the heat source is applied to the interior surface of the enclosure.

13. The method of attaching an end seal to a manufactured seed of claim 11, wherein the heat source is a laser beam applied to the interior surface of the enclosure.

14. The method of attaching an end seal to a manufactured seed of claim 11, wherein the step of pressurizing a sealing material includes supplying a predetermined volume of a fluid to the sealing material.

15. The method of attaching an end seal to a manufactured seed of claim 14, wherein the predetermined volume of a fluid expands the sealing material forming the enclosure to define a predetermined burst strength for the enclosure.

16. The method of attaching an end seal to a manufactured seed of claim 15, wherein the enclosures include a substantially constant thickness.

17. The method of attaching an end seal to a manufactured seed of claim 14, further comprising maintaining the predetermined volume of a fluid within the enclosure for a predetermined period of time.

18. The method of attaching an end seal to a manufactured seed of claim 17, further comprising exhausting a portion of the predetermined volume of a fluid within the enclosure to define a predetermined second volume of a fluid within the enclosure.

19. The method of attaching an end seal to a manufactured seed of claim 18, wherein attaching the enclosure to the manufactured seed includes applying a laser beam to the interior surface of the enclosure.

* * * * *